United States Patent
Jun et al.

(10) Patent No.: US 8,395,004 B2
(45) Date of Patent: Mar. 12, 2013

(54) PROCESS FOR PRODUCING LIGHT OLEFINS FROM SYNTHESIS GAS USING DUAL SEQUENTIAL BED REACTOR

(75) Inventors: Ki-won Jun, Daejeon (KR); Yun-Jo Lee, Daejeon (KR); Jong-Wook Bae, Daejeon (KR); Jo Yong Park, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 388 days.

(21) Appl. No.: 12/739,217

(22) PCT Filed: Sep. 22, 2008

(86) PCT No.: PCT/KR2008/005606
§ 371 (c)(1), (2), (4) Date: Apr. 22, 2010

(87) PCT Pub. No.: WO2009/054616
PCT Pub. Date: Apr. 30, 2009

(65) Prior Publication Data
US 2010/0261940 A1    Oct. 14, 2010

(30) Foreign Application Priority Data
Oct. 26, 2007  (KR) .......................... 10-2007-0108494

(51) Int. Cl.
*C07C 4/06* (2006.01)
*C07C 27/00* (2006.01)

(52) U.S. Cl. .................... 585/324; 585/653; 518/719

(58) Field of Classification Search .................. 585/324, 585/653; 518/719
See application file for complete search history.

(56) References Cited

U.S. PATENT DOCUMENTS

| | | | |
|---|---|---|---|
| 4,544,674 A * | 10/1985 | Fiato et al. ..................... | 518/717 |
| 5,026,936 A | 6/1991 | Leyshon et al. | |
| 5,371,308 A | 12/1994 | Gosselink et al. | |
| 6,106,697 A | 8/2000 | Swan et al. | |
| 6,258,257 B1 | 7/2001 | Swan, III et al. | |
| 7,531,706 B2 | 5/2009 | Wakui et al. | |
| 2006/0178546 A1 * | 8/2006 | Mo et al. ........................ | 585/648 |
| 2007/0083071 A1 | 4/2007 | Choi et al. | |

FOREIGN PATENT DOCUMENTS

| | | | |
|---|---|---|---|
| EP | 0109059 | * | 5/1984 |
| KR | 10-2001-0043239 A | | 5/2001 |
| KR | 10-2002-0049056 A | | 6/2002 |
| WO | WO 2004/067486 A | | 8/2004 |
| WO | WO 2006/070006 A | | 7/2006 |

* cited by examiner

*Primary Examiner* — Thuan D Dang
(74) *Attorney, Agent, or Firm* — Frommer Lawrence & Haug LLP; Ronald R. Santucci

(57) ABSTRACT

The present invention relates to a process for producing light olefins from a synthesis gas with significantly improved conversion and selectivity for $C_2$-$C_4$ light olefins in general and propylene in particular, as compared to a conventional process, through a sequential two-step process comprising preparing olefin compounds from a synthesis gas in the presence of an iron catalyst by the Fischer-Tropsch reaction followed by cracking the olefin compounds in the presence of a zeolite catalyst.

6 Claims, 1 Drawing Sheet

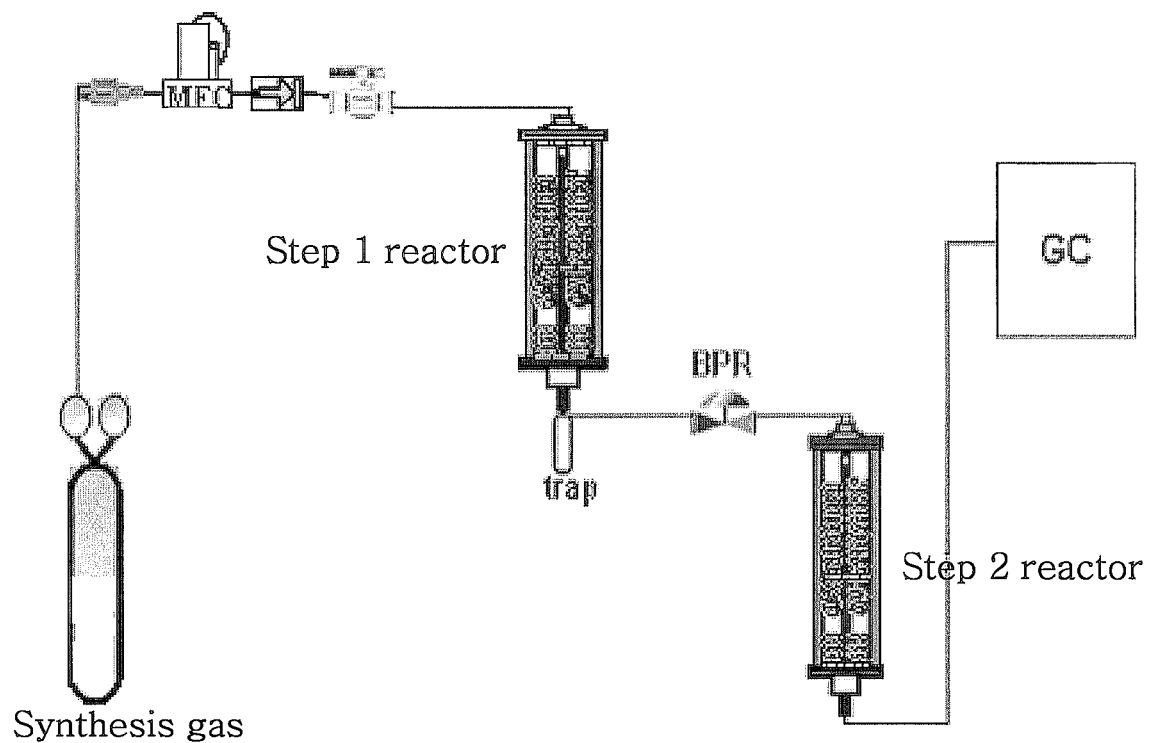

PROCESS FOR PRODUCING LIGHT OLEFINS FROM SYNTHESIS GAS USING DUAL SEQUENTIAL BED REACTOR

This application is a 371 of PCT/KR2008/005606 filed on Sep. 22, 2008 published on Apr. 30, 2009 under publication number WO 2009/054616 A which claims priority benefits to Korean Patent Application Number 10-2007-0108494 filed Oct. 26, 2007.

TECHNICAL FIELD

The present invention relates to a process for producing light olefins from a synthesis gas with significantly improved conversion and selectivity for $C_2$-$C_4$ light olefins, in particular, propylene, as compared to a conventional process, through a sequential two-step process comprising preparing olefin compounds from a synthesis gas in the presence of an iron catalyst by the Fischer-Tropsch reaction and cracking the olefin compounds in the presence of a zeolite catalyst.

BACKGROUND ART

In general, light olefins are produced by a contact cracking process in which naphtha, a gasoline component obtained from distillation of petroleum at normal pressure, is thermally cracked at 750-850° C. to produce a basic source of petrochemicals, including ethylene, propylene, benzene, and the like.

Especially, ethylene and propylene are used in various fields. Specifically, ethylene is used to produce various useful materials including vinyl chloride, polyethylene, acetic acid, synthetic paints, etc., due to its high reactivity. Propylene is obtained from a liquefied petroleum gas and is used as a raw material for the production of polymer gasoline and other petrochemicals, including isopropyl alcohol, acetone, propylene oxide, propylene glycol, allyl alcohol, glycerol, acrylonitrile, phenol acetone, dodecylbenzene, and the like. Besides, it is used to produce polypropylene through addition polymerization reaction, which is used to prepare a synthetic fiber.

Therefore, development of a process for the production of light olefins with superior yield and selectivity is highly required.

A commonly used technique to improve the selectivity for light olefins is to increase the thermal cracking reactions at higher reaction temperatures. However, at elevated reaction temperatures, the catalysts exhibit inferior long-term stability and feed conversions. Moreover, the high temperature operation can cause an accelerated coke generation on the catalyst that eventually leads to a lower catalytic activity and lower feeding rate of raw material. These factors can limit the production of ethylene and propylene at high yields. Another method to improve selectivity for light olefins is to add a chemical component to modify the activity of the catalyst. One such example is the modification of cracking activity of the ZSM-catalyst by adding phosphorus so as to convert the primary cracking product into $C_2$-$C_4$ light olefins.

At present, many research groups are actively working for the production of light olefins through cracking reactions.

Korean Patent Publication No. 2002-7006467 discloses a highly efficient catalyst composite for the production of light olefins through a conventional fluid catalytic cracking (FCC) process. The catalyst composition selective for olefins is prepared by treating a zeolite catalyst with a compound containing 10 wt % $P_2O_5$.

Korean Patent Publication No. 2000-7012182 discloses a cracking process for selectively producing $C_2$-$C_4$ light olefins. First, the gas oil and residual oil feeds are converted in a zeolite based FCC process to obtain low boiling point products that include a hydrocarbon stream that boils in naphtha range. Then, the products are fractionated based on boiling points and only the naphtha boiling range stream is transferred to the second step. A product resultant from the second step reaction is stripped to obtain $C_2$-$C_4$ light olefins with high selectivity. The principle involved in the currently employed contact cracking process is to provide a fluid contact between the thermally pre-treated feed and a heated catalyst for the cracking reaction (fluid contact). The fluid contact technique requires a stripping process for removing coke and other hydrocarbon materials because they may adhere to the catalyst particles during cracking and result in reduced catalytic activity and selectivity.

U.S. Unexamined Patent Application No. 2006/0116544 A1 discloses a catalyst for producing olefins with high selectivity and yield, where a catalyst comprising pentasil type zeolite containing rare earth element is used to improve light olefin selectivity in catalytic cracking.

U.S. Pat. No. 5,026,936 discloses a method for improving selectivity for propylene using a two-step reactor. In the first step, propylene, ethylene and butane are produced in high yield from a hydrocarbon feed through catalytic cracking. After separating the propylene from the product stream, ethylene and butene are further treated in the second step for the production of propylene through olefin metathesis reaction.

U.S. Unexamined Patent Application No. 2007/0083071 discloses a zeolite based process that operates in a fixed or fluidized-bed reactor for the production of light olefins. While supplying a catalyst periodically or continuously into a catalytic cracking reactor, a hydrocarbon feed and steam are fed into the reactor to carry out cracking. The product is separated based on the boiling point, and $C_2$-$C_3$ paraffinic hydrocarbons are recovered for undergoing thermal cracking to produce $C_2$-$C_3$ olefins. $C_4$ or higher hydrocarbons are recycled to the catalytic cracking step along with a feedstock.

U.S. Pat. Nos. 6,106,697 and 6,258,257 disclose a two-step process for improving yield of light olefins. In the first step, gas oil or residual oil (resid) is reacted in a FCC unit containing a large pore zeolite catalyst to produce a mixture of hydrocarbons. In the second step, the hydrocarbons are passed through a reaction zone, a stripping zone and a catalyst regeneration zone to improve selectivity for $C_2$-$C_4$ olefins.

In the aforesaid techniques, FCC process is used for the production of light olefins and the selectivity to light olefins is improved by recycling the undesired product or treating the product stream after the separation of light olefins. However, the cracking reaction is sensitive to various catalysts and process parameters such as reaction temperature, activity of the catalyst and contact time, etc., that requires a precise control to optimize such parameters for selective production of ethylene and propylene.

DISCLOSURE

Technical Problem

Because the conventional method for producing light olefins is complicated and involves separate processes, the present invention is aimed to develop a simplified process for producing light olefins with improved selectivity and conversions, through a sequential two-step catalytic reaction.

Technical Solution

The present invention provides a sequential two-step process for producing light olefins from a synthesis gas comprising a first step of performing a Fischer-Tropsch reaction of a synthesis gas at 200-400° C., 5-25 atm with a feed flow rate of 500-8,000 GHSV in the presence of an iron catalyst so as to produce as much olefin compounds as possible, and a second step of cracking the olefin compounds at 300-700° C., 0.1-5 atm in the presence of a zeolite catalyst to produce $C_2$-$C_4$ light olefins.

ADVANTAGEOUS EFFECTS

The present invention provides a process for producing light olefins from a synthesis gas using a sequential two-step catalytic reactor. The process is expected to be useful in various industrial fields because it provides superior conversion and selectivity for $C_2$-$C_4$ light olefins, in particular, propylene.

DESCRIPTION OF DRAWING

The above and other features of the present invention will now be descried in detail with reference to certain example embodiments thereof illustrated in the accompanying drawing which is given hereinbelow by way of illustration only, and thus is not limitative of the present invention, and wherein:

FIG. 1 schematically illustrates a two-step catalytic reactor according to the present invention. It comprises a step 1 reactor for Fischer-Tropsch reaction and a step 2 reactor for cracking of olefins. A trap is equipped below each reactor.

BEST MODE

Hereinafter, reference will be made in detail to various embodiments of the present invention, examples of which are illustrated in the accompanying drawing and described below. While the invention will be described in conjunction with example embodiments, it will be understood that the present description is not intended to limit the invention to those example embodiments. On the contrary, the invention is intended to cover not only the examplary embodiments, but also various alternatives, modifications, equivalents and other embodiments, which may be included within the spirit and scope of the invention as defined by the appended claims.

The present invention relates to a process for producing light olefins from a synthesis gas with significantly improved conversion and selectivity for $C_2$-$C_4$ light olefins, in particular, propylene, as compared to a conventional process even without an additional separation process, through a sequential two-step process comprising preparing hydrocarbon compounds from a synthesis gas in the presence of an iron catalyst by the Fischer-Tropsch reaction and cracking the hydrocarbon compounds in the presence of a zeolite catalyst.

In the first step of performing Fischer-Tropsch reaction for conversion of a synthesis gas to hydrocarbons, an iron catalyst containing copper and other transition metals and potassium is used to maximize the proportion of heavy olefins in the total hydrocarbons while preventing the production of methane. The reaction is carried out at a relatively high temperature so as to enhance conversion of the synthesis gas and yield of olefins. Reaction conditions such as pressure and flow rate are varied to improve yield and selectivity of olefins.

In the second step of olefin cracking, a silica-rich zeolite catalyst having excellent reaction activity and superior selectivity for light olefins, particularly a ZSM-5 catalyst, which has superior selectivity for propylene, high resistance to coke generation, low acid density and high Si/Al ratio, is used as catalyst so as to ensure high propylene selectivity and good catalyst stability against coke generation.

Referring to FIG. 1, the two-step catalytic reaction process will be described in detail. Two reactors are sequentially connected. A catalyst is packed inside a step 1 reactor. Outside of the reactor, a heater is connected so that temperature can be controlled. Below the reactor, a trap is equipped so as to store the hydrocarbon product. Through a pipe, the trap is connected to a step 2 reactor. Between the step 1 reactor and the step 2 reactor, a back pressure regulator (BPR) is equipped so as to control the pressure of each reactor. The lines connecting the trap to other area can be heated using a heating wire so as to prevent condensation. The step 2 reactor is structurally identical to the step 1 reactor. A line from the trap is connected to GC (gas chromatography) so as to confirm the progress of reaction.

Hereinafter, the process for producing light olefins from a synthesis gas according to the present invention will be described in detail.

In the first step, hydrocarbon compounds are produced from a synthesis gas by Fischer-Tropsch reaction in the presence of an iron catalyst.

The iron catalyst may be one commonly used in the related art and is not specially limited. A catalyst comprising 60-95 wt % iron may be used. If the iron content is less than 60 wt %, reaction activity and olefin yield may decrease. In contrast, if the iron exceeds 95 wt %, the production of methane and paraffin may increase. Hence, it is preferred that the aforesaid range be maintained. And, the iron catalyst may comprise 0.01-0.1 mol of a metal selected from copper, manganese, chromium, vanadium and zinc as cocatalyst component based on 1 mol of iron. If the content of the cocatalyst component is less than 0.01 mol, the production of methane and paraffin may increase. In contrast, if the content of the cocatalyst component exceeds 0.1 mol, reaction activity and olefin yield may decrease. Hence, it is preferred that the aforesaid range be maintained.

Further, an oxide such as alumina, silica, magnesia, titania, etc., may be used as a support, and the catalyst is treated with a potassium-containing compound so as to improve selectivity for olefins and inhibit the production of methane. The potassium-containing compound may be one commonly used in the related art. It may be potassium nitrate, potassium carbonate, etc., and may be used in an amount of 0.01-0.2 mol based on 1 mol of iron.

The iron catalyst may be activated by reducing at 350-450° C. and normal pressure for 1-24 hours under hydrogen atmosphere prior to use. The activation is commonly used in the related art, and the aforesaid condition is recommended for effective reduction.

For the synthesis gas, a 1:1-3 (v/v), preferably 1:1.5-2.5, a mixture of carbon monoxide and hydrogen may be used. If the volume proportion of hydrogen is less than 1, conversion may decrease. In contrast, if the volume proportion of hydrogen exceeds 3, the production of methane and paraffin may increase. Hence, it is preferred that the aforesaid range be maintained.

The reaction is carried out at 200-400° C., preferably 250-350° C., and 5-25 atm, preferably 10-20 atm, and at a flow rate of 500-8,000 GHSV, preferably 1,000-6,000 GHSV. If the reaction temperature is below 200° C., conversion and olefin yield may decrease. In contrast, if the reaction temperature exceeds 400° C., the catalyst may be deactivated quickly. If the reaction pressure is below 5 atm, conversion may decrease. In contrast, if the reaction pressure exceeds 25 atm, the production of paraffin may increase. If the flow rate is below 500 GHSV, productivity may decrease. And, if the flow rate exceeds 8,000 GHSV, conversion may decrease. Hence, it is preferred that the aforesaid range be maintained.

Thus produced olefins have selectivity of 50-90 carbon mol %. Selectivity for methane is maintained at the level of not more than 30 carbon mol %, preferably not more than 20 carbon mol %.

For the reactor, a reactor commonly used in the related art may be used. Specifically, a fixed-bed reactor, a fluidized-bed reactor or a slurry reactor may be used.

In the first step, the synthesis gas is converted to hydrocarbon compounds by Fischer-Tropsch reaction. The produced hydrocarbon compounds include unsaturated olefin compounds and saturated paraffin compounds. All the produced hydrocarbon compounds are transferred to the second step where continuous cracking is carried out, without an additional purification process. Of the hydrocarbon compounds, only olefins undergo reaction. At this stage, the reaction temperature is controlled for facilitating the selective cracking of olefins. Paraffins undergo reaction at higher temperature, typically 750-900° C. The hydrocarbon compounds produced in the first step include those of low boiling point and those of high boiling point. Hydrocarbon compounds having a low boiling point are in the gaseous form and can be transferred to the second reactor. But, those having a high boiling point should be sufficiently heated. By controlling the temperature of the trap, the hydrocarbons having a high boiling point are also transferred to the step 2 reactor as gas. Cracking reaction in the second reactor facilitates the formation of low molecular weight hydrocarbons. In order to improve the yield of $C_2$-$C_4$ light olefins, it is preferred that all the hydrocarbons produced in the first step are transferred to the step 2 reactor for the cracking. To this end, the temperature of the trap is maintained at 140-200° C.

Next, the hydrocarbon compounds are cracked in the presence of a zeolite catalyst to prepare $C_2$-$C_4$ light olefins.

The zeolite catalyst may be one commonly used in the related art. Natural or synthetic zeolite can be used without special limitation. But, specifically, ZSM-5 having an MFI structure may be used. Particularly, one comprising 80-6,000 mols, preferably 120-4000 mols of $SiO_2$ for 1 mol of $Al_2O_3$ may be used. If the $SiO_2$ content is less than 80 molar equivalents, H-transfer reaction occurs actively because of increased acid density and reactivity of the catalyst. As a result the selectivity to paraffins and aromatic compounds increase with simultaneous decrease of olefin selectivity. And, if the $SiO_2$ content is more than 6,000 molar equivalents, olefin cracking does not occur to a desired extent due to the decrease in the number of reaction active sites. Hence, it is preferred that the aforesaid range be maintained.

The acid characteristics such as acid strength, density of zeolites can be changed by treating the zeolite with a phosphorus (P)-containing compound, e.g., phosphoric acid, ammonium phosphate [$(NH_4)H_2PO_4$ or $(NH_4)_2HPO_4$], etc., to improve the olefin selectivity and enhance hydrothermal stability of the zeolite catalyst. The acid property may be further controlled and the hydrothermal stability of the zeolite can be improved by treating with a lanthanum-containing compound, e.g., lanthanum nitrate, lanthanum chloride, etc. The phosphorus or lanthanum compound may be used in an amount of 0.01-10 wt % based on the zeolite. Preferably, the phosphorus compound may be used in an amount of 0.01-2.5 wt %, and the lanthanum compound may be used in an amount of 0.01-10 wt %, based on the zeolite.

The phosphorus-containing zeolite may be prepared by first impregnating a phosphorus compound, on zeolite followed by its drying at 100-120° C., and then baking at 400-700° C. for 5-12 hours. The phosphorus- and lanthanum-containing zeolite may be prepared by further impregnating a lanthanum compound on the phosphorus-containing zeolite followed by drying the same at 100-120° C., and then baking at 400-700° C. for 5-12 hours.

Hydrothermal stability of the zeolite is an important factor for catalyst development. Water produced during the Fischer-Tropsch reaction and the occasional addition of water conducted during the reaction to prevent coke formation, are the two main sources of water that can affect the hydrothermal stability. Especially at high temperatures water can expel aluminum from the zeolite framework (dealumination), resulting in permanent loss of acid sites.

In case water is used in the second step, it is used in an amount of 0.01-1 part by weight based on 1 part by weight of the hydrocarbon compounds. If water is used in an amount of less than 0.01 part by weight, the catalyst may be deactivated due to coke generation. In contrast, if water is used in an amount more than 1 part by weight, dealumination may occur, thereby resulting in permanent deactivation of the catalyst. Hence, it is preferred that the aforesaid range be maintained.

The reaction is carried out at 300-700° C., preferably 400-600° C., at 0.1-5 atm, and at a flow rate of 1,500-30,000 GHSV. If the reaction temperature is below 300° C., the olefin source may remain unreacted, thereby resulting in decreased yield of ethylene and propylene. In contrast, if the reaction temperature is above 700° C., coke generation may be accelerated during olefin cracking, thereby resulting in fast decrease of catalytic activity that eventually demands the reduced feed rate of the source material. Further, the enhanced formation of undesired byproducts such as hydrogen, saturated hydrocarbons and aromatic hydrocarbons suppresses the formation of desired olefins such as ethylene and propylene. When the reaction pressure is below 0.1 atm, conversion decreases. When the reaction pressure exceeds 5 atm, coke generation may increase. Hence, it is preferred that the aforesaid range of reaction pressure may be maintained. Similarly, at lower flow rates below 1,500 GHSV, the olefin selectivity decreases and at higher flow rates exceeding 30,000 GHSV, the conversion may decrease. Hence, it is preferred that the aforesaid range of feed flow rate may be maintained.

Thus the product at optimized reaction conditions exhibits selectivity of 30-65 carbon mol % of $C_2$-$C_4$ light olefins and 10-35 carbon mol % for propylene.

MODE FOR INVENTION

Hereinafter, the present invention is described in detail with reference to examples. However, the present invention is not limited by the examples.

Preparation of Iron Catalyst

Preparation Example 1

An aqueous metal solution prepared by dissolving 51.4 g of $Fe(NO_3)_3.9H_2O$, 2.02 g of $Cu(NO_3)_2.6H_2O$ and 15.88 g of $Al(NO_3)_3.6H_2O$ in 250 mL of water was titrated with an aqueous sodium carbonate solution prepared by dissolving 25.58 g of $Na_2CO_3$ in 250 mL of water, at 70° C. and a rate of 100 mL/h while stirring. After stirring for 2 hours at the same temperature, the solution was cooled to room temperature (20° C.). The precipitate formed by the cooling was washed 3 times with 70° C. of water, dried at 110° C. for 12 hours, and baked at 500° C. for 6 hours to obtain an Fe—Cu—$Al_2O_3$ catalyst.

Preparation Example 2

After preparing a catalyst comprising 6 parts of copper and 16 parts of alumina by weight, based on 100 parts of iron by weight, in the same manner as Preparation Example 1, a K/Fe—Cu—$Al_2O_3$ catalyst comprising 6 parts of potassium by weight was prepared using potassium nitrate as a potassium precursor.

Preparation Example 3

An Fe—K catalyst comprising 6 parts of potassium by weight, based on 100 parts of iron by weight, was prepared in the same manner as Preparation Example 1, using potassium nitrate as a potassium precursor.

Preparation Example 4

A catalyst comprising iron only was prepared in the same manner as Preparation Example 1.

Preparation of Zeolite Catalyst

Preparation Example 5

ZSM-5 ($SiO_2/Al_2O_3$=280, molar ratio) zeolite catalyst.

Preparation Example 6

A P/ZSM-5 ($SiO_2/Al_2O_3$=280, molar ratio) catalyst further comprising phosphorus was prepared from the zeolite catalyst of Preparation Example 5.

Preparation Example 7

A 0.25 wt % P/1.1 wt % La/ZSM-5 ($SiO_2/Al_2O_3$=280, molar ratio) catalyst further comprising 0.25 wt % of phosphorus and 1.1 wt % of lanthanum (La) was prepared from the zeolite catalyst of Preparation Example 5.

Preparation Example 8

ZSM-5 ($SiO_2/Al_2O_3$=23, molar ratio) zeolite catalyst.

EXAMPLES

Preparation of Light Olefins from Synthesis Gas

Example 1

The iron catalyst of Preparation Example 2 was put in a step 1 reactor, and reduced by activating at normal pressure and 450° C. for 12 hours under hydrogen atmosphere. Then, under a condition of 300° C. and 10 atm, a synthesis gas having a $CO/H_2$ ratio of 2 was flown at a flow rate of 6000 GHSV to prepare hydrocarbon compounds. The produced hydrocarbon compounds were transferred to a trap, and the trap was maintained at 120° C. The produced hydrocarbon compounds were immediately transferred to a step 2 reactor in which the zeolite catalyst of Preparation Example 5 was packed, and light olefins were prepared by carrying out cracking at 500° C. and normal pressure.

Conversion and selectivity of the prepared light olefins are summarized in Table 1 below.

Example 2

Light olefins were prepared in the same manner as Example 1, with the temperature of the step 2 reactor changed to 400° C. Conversion and selectivity of the prepared light olefins are summarized in Table 1.

Example 3

Light olefins were prepared in the same manner as Example 1, with the temperature of the step 2 reactor changed to 600° C. Conversion and selectivity of the prepared light olefins are summarized in Table 1.

Example 4

Light olefins were prepared in the same manner as Example 1, with the temperature of the trap during the first step changed to 200° C. Conversion and selectivity of the prepared light olefins are summarized in Table 1.

Example 5

Light olefins were prepared in the same manner as Example 1, with the temperature of the trap during the first step changed to 180° C. Conversion and selectivity of the prepared light olefins are summarized in Table 1.

Example 6

Light olefins were prepared in the same manner as Example 1, with the temperature of the trap during the first step changed to 160° C. Conversion and selectivity of the prepared light olefins are summarized in Table 1.

Example 7

Light olefins were prepared in the same manner as Example 1, with the temperature of the trap during the first step changed to 140° C. Conversion and selectivity of the prepared light olefins are summarized in Table 1.

Example 8

Light olefins were prepared in the same manner as Example 1, using the zeolite catalyst of Preparation Example 6 in the second step. Conversion and selectivity of the prepared light olefins are summarized in Table 1.

Example 9

Light olefins were prepared in the same manner as Example 1, using the zeolite catalyst of Preparation Example 7 in the second step. Conversion and selectivity of the prepared light olefins are summarized in Table 1.

Example 10

Light olefins were prepared in the same manner as Example 1, using water in the second step with an amount of $H_2O/CO$=0.5 (molar ratio), based on the synthesis gas in the first step. Conversion and selectivity of the prepared light olefins are summarized in Table 1.

Example 11

Light olefins were prepared in the same manner as Example 1, with the pressure in the second step changed to 3 atm. Conversion and selectivity of the prepared light olefins are summarized in Table 1.

Example 12

Light olefins were prepared in the same manner as Example 1, with the flow rate in the first step changed to 2,000

GHSV. Conversion and selectivity of the prepared light olefins are summarized in Table 1.

Example 13

Light olefins were prepared in the same manner as Example 1, with the temperature in the first step changed to 275° C. Conversion and selectivity of the prepared light olefins are summarized in Table 1.

Comparative Example 1

Light olefins were prepared in the same manner as Example 1, with the temperature in the second step changed to 300° C. Conversion and selectivity of the prepared light olefins are summarized in Table 1.

Comparative Example 2

Light olefins were prepared in the same manner as Example 1, using only the first step of preparing the hydrocarbon compounds. Conversion and selectivity of the prepared light olefins are summarized in Table 1.

Comparative Example 3

Light olefins were prepared in the same manner as Example 1, using the zeolite catalyst of Preparation Example 3 in the second step. Conversion and selectivity of the prepared light olefins are summarized in Table 1.

Comparative Example 4

Light olefins were prepared in the same manner as Example 1, using the zeolite catalyst of Preparation Example 4 in the second step. Conversion and selectivity of the prepared light olefins are summarized in Table 1.

Comparative Example 5

Light olefins were prepared in the same manner as Example 1, using the zeolite catalyst of Preparation Example 8 in the second step. Conversion and selectivity of the prepared light olefins are summarized in Table 1.

TABLE 1

| | | Selectivity (%) | |
| --- | --- | --- | --- |
| | Conversion (%) | Light olefins ($C_2$-$C_4$) | Propylene |
| Example 1 | 95.5 | 39.0 | 18.7 |
| Example 2 | 95.6 | 32.8 | 13.8 |
| Example 3 | 77.1 | 29.8 | 15.4 |
| Example 4 | 95.2 | 62.3 | 29.5 |
| Example 5 | 95.4 | 55.2 | 26.9 |
| Example 6 | 95.4 | 46.1 | 22.2 |
| Example 7 | 95.2 | 42.0 | 20.1 |
| Example 8 | 92.6 | 42.6 | 20.6 |
| Example 9 | 96.4 | 44.0 | 21.1 |
| Example 10 | 95.4 | 37.1 | 19.5 |
| Example 11 | 95.6 | 35.2 | 16.8 |
| Example 12 | 97.5 | 43.5 | 20.4 |
| Example 13 | 65.1 | 42.2 | 21.6 |
| Comparative Example 1 | 95.6 | 23.1 | 7.1 |
| Comparative Example 2 | 95.4 | 23.4 | 8.9 |
| Comparative Example 3 | 45.1 | 11.4 | 5.7 |
| Comparative Example 4 | 37.2 | 6.8 | 3.9 |
| Comparative Example 5 | 95.3 | 23.4 | 11.4 |

As shown in Table 1, selectivity for light olefins and propylene are superior in Examples 1-13 than Comparative Examples.

The invention has been described in detail with reference to preferred embodiments thereof. However, it will be appreciated by those skilled in the art that changes may be made in these embodiments without departing from the principles and spirit of the invention, the scope of which is defined in the accompanying claims and their equivalents.

The invention claimed is:

1. A sequential two-step process for producing light olefins from a synthesis gas comprising:
    a first step of performing a Fischer-Tropsch reaction of a synthesis gas at 200-400° C. and 5-25 atm and a flow rate of 500-8,000 GHSV in the presence of an iron catalyst to produce hydrocarbon compounds, wherein the iron catalyst comprises 0.01-0.1 mol of a metal selected from the group consisting of: copper, manganese, chromium, vanadium and zinc, based on 1 mol of iron, and, wherein the hydrocarbon compounds produced comprise 50-90 carbon mol % of olefin compounds; and
    a second step of cracking all the hydrocarbon compounds produced in the first step at 300-700° C. and 0.1-5 atm in the presence of a zeolite catalyst to produce $C_2$-$C_4$ light olefins, wherein the hydrocarbon compounds produced in the first stet) are not purified prior to the second step of cracking.

2. The preparation process according to claim 1, wherein the iron catalyst comprises 60-95 wt % of iron.

3. The preparation process according to claim 1, wherein the zeolite catalyst is a ZSM-5 zeolite catalyst comprising 80-6,000 mol of $SiO_2$ based on 1 mol of $Al_2O_3$.

4. The preparation process according to claim 1, wherein the zeolite catalyst comprises 0.01-0 wt % of phosphorus (P), lanthanum (La) or a mixture thereof, based on zeolite.

5. The preparation process according to claim 1, wherein, in the second step, 0.01-1 part of water by weight is further added based on 1 part by weight of the hydrocarbon compounds.

6. The preparation process according to claim 1, wherein the produced $C_2$-$C_4$ light olefins have selectivity of 30-65 carbon mol %, and 10-35 carbon mol % for propylene.

* * * * *